United States Patent [19]

Mikkelsen

[11] Plant 4,204

[45] Jan. 31, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,525

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel impatiens plant having large foliage and medium red to orange red flowers, and which grows well in full sunlight.

1 Drawing Figure

1

The present invention relates to a new and distinctive cultivar of Impatiens plant, botanically known as Impatiens and known by the cultivar name Paul Revere. The new cultivar was developed by me though controlled breeding by crossing an unpatented selected New Guinea Impatiens seedling number 74-200-8 (seed parent) with unpatented seedling number 74-108-1 (pollen parent). Both seedlings were developed by me from previous pollinations. Asexual reproduction of terminal or stem cuttings has shown that the unique features of this new Impatiens variety are stabilized and are reproduced true to type in successive propagations.

The following characteristics distinguish the new Impatiens from other cultivated Impatiens of this type known and used in the floriculture industry:

1. Large variegated foliage having dark green outer areas and light yellow green inner areas near the midrib. Young foliage is heavily rippled but at maturity the foliage appears only rugose.

2. Medium red to orange red flowers up to 6 cm. in diameter.

3. Upright medium height plant with good self branching habits forming a symmetrical herb. Paul Revere has excellent potential as a pot plant.

4. Grows and flowers in full sunlight outdoors without deterioration of flowers or the variegated foliage, in comparison to Impatiens Sultani which are generally grown in semi-shaded areas.

5. Plant growth and flower development of this cultivar require higher levels of nutrients than Impatiens Sultani.

The accompanying colored photograph illustrates the overall appearance of the new cultivar, and shows the colors as true as it is reasonably possible to obtain in a colored reproduction of this type.

The following is a detailed description of my new Impatiens cultivar based on plants produced under commercial practices in the greenhouses of Mikkelsens Inc., Ashtabula, Ohio, during September, 1976. Color references are made to the Royal Horticultural Society Colour Chart except where general terms of ordinary dictionary significance are used.

Parentage: A controlled cross of Impatiens seedling No. 74-200-8 with Impatience seedling No. 74-108-1, both of which were developed by me in previous pollinations.

Propagation:

*Type cutting.*—Terminal cuttings.

*Time to root.*—10 days at 20°-21° C summer.

2

*Rooting habit.*—Typical for Impatiens, rapid, dendritic and very abundant in primary and secondary roots.

Plant description:

*Form.*—A semi-compact, medium height, upright herb.

*Habit of growth.*—Moderately self branching, being contained, upright; vigorous strong stems; does not sprawl.

*Foliage.*—The initial foliage is predominately green; as the plant matures the terminal foliage becomes variegated, whorled 6-8 leaves at nodes. Size: Varies depending on the number of growing shoots in any given unit of space; from 5-6 cm. wide by 12-14 cm. long with petiole up to 5 cm. long. Shape: Near elliptical to oblanceolate, revolute, apex acuminate, base acute, pinnately veined. Texture: Glabrous, rugose. Margin: Nearly entire, ciliolate. Color: Young foliage, top side green 137B, under side yellow green near 148B; mature foliage, top side of outer area darker than yellow green 147A; inner area from yellow 3C blending to yellow green to green; under side of outer area yellow green near 147B; inner area yellow green 151C. Venation: Pinnately, arcuate.

Flowering description:

*Flowering habits.*—Flowers open consecutively around the whorl of the leaves at nodes; consistently one flower per leaf as each leaf matures.

*Natural flowering season.*—Flowering is indeterminate and occurs throughout the year on mature plants regardless of day length. Juvenile vegetative cuttings apparently must pass through aging process before flowering begins.

*Flower bud description.*—Flower buds are pyramidal covered with three sepals and an emerging spur that curves around the bud, unfolding as the bud opens.

*Flowers borne.*—Single flowers borne on a pedicel 5-8 cm. long.

*Quantity of flowers.*—6-8 per whorl of leaves when flowering develops after mature growth.

*Petals.*—Shape: Nearly rectangular, outer edge emarginate. Color: Top side in winter when opening red between 40A-B fading to red 40C; under side red 43C. Number of petals: Five. Size of petals: Petals 2 × 3 cm.; total flower diameter 5-6 cm. Curved spur is red 53B, between 4-5 cm. long.

*Reproductive organs.*—Stamens: One in number. Anther shape; Hooded, color red 53B. Pollen color: cream white. Pistils: Stigma: Shape is circular, flat, having irregular surface, color green. Style color: Light green. Ovaries: One, size 2–3 mm. long before fertilized, color green.

I claim:

1. A new and distinct cultivar of Impatiens known by the cultivar name Paul Revere and particularly characterized as to uniqueness by the combined characteristics of large variegated foliage having dark green outer areas and light green inner areas near the midrib; medium red to orange red flowers up to 6 cm. in diameter; upright medium height plant with good self branching habits and by its growing and flowering in full sunlight outdoors without deterioration of flower or the variegated foliage.

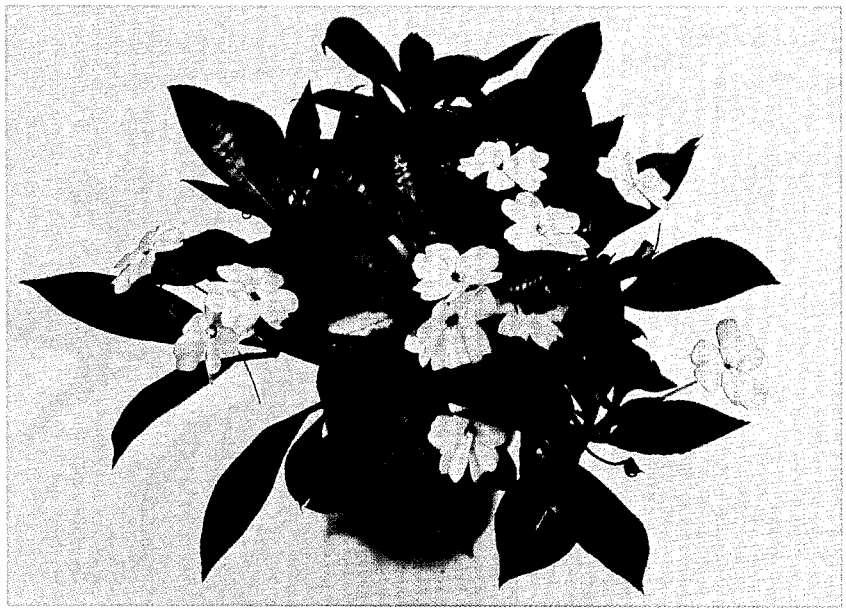

* * * * *